United States Patent [19]

Drent

[11] Patent Number: 4,599,476
[45] Date of Patent: Jul. 8, 1986

[54] PROCESS FOR THE PREPARATION OF DIMERIZATION PRODUCTS FROM OLEFINS

[75] Inventor: Eit Drent, Amsterdam, Netherlands

[73] Assignee: Shell Oil Company, Houston, Tex.

[21] Appl. No.: 783,706

[22] Filed: Oct. 3, 1985

[30] Foreign Application Priority Data

Dec. 19, 1984 [NL] Netherlands .......................... 8432042

[51] Int. Cl.⁴ ............................................. C07C 2/26
[52] U.S. Cl. .................................... 585/511; 585/510
[58] Field of Search ........................ 585/510, 511, 531

[56] References Cited
FOREIGN PATENT DOCUMENTS 1153519  5/1969  United Kingdom .
 374930  9/1978  U.S.S.R. .

OTHER PUBLICATIONS

Chem. Abstr. 90 22286 h (1979).
J. Am. Chem. Soc. 103 4627–4629 (1981) and 104 3520–3522 (1982).
Transition Metal Catalyzed Polymerization; Alkenes and Dienes, Part A, ed. by R. P. Quirk, 1983, pp. 341–354.
Angew, Chem. Int. Ed. 14 (1975) 104–105.

Primary Examiner—Curtis R. Davis

[57] ABSTRACT

A process for the preparation of dimerization products from aliphatic mono-olefins having 2 to about 12 carbon atoms in which the aliphatic mono-olefin is contacted with a catalytic system formed by combining a palladium and/or ruthenium compound and an acid with a pKa of less than 2, except hydrohalogenic acids in an aprotic organic solvent.

16 Claims, No Drawings

PROCESS FOR THE PREPARATION OF DIMERIZATION PRODUCTS FROM OLEFINS

FIELD OF THE INVENTION

The present invention relates to a process for the preparation of dimerization products from low molecular weight aliphatic mono-olefins using a catalyst containing palladium and/or ruthenium in an organic solvent.

BACKGROUND OF THE INVENTION

It has been suggested that ethene can be dimerized to butenes in a reaction medium consisting of highly concentrated strong mineral acids such as phosphoric acid (concentration 14.0 mol/l, ~85%) and sulfuric acid (concentration 17.0 mol/l, ~95%) using as catalyst a palladium salt with an anion which has little or no interaction with the palladium. This dimerization is not attractive, however, because it combines a highly corrosive reaction medium with a very low conversion rate of ethene to butenes relative to the amount of palladium (cf.: USSR Patent Specification No. 374930 [Chem. Abstr. 90 22286 h]).

Further, it is known that ethene can be dimerized in chloroform using as catalyst the compound [Pd(CH$_3$CN)(PPh$_3$)$_3$] (BF$_4$)$_2$ or the compounds [Pd(CH$_3$CN)$_4$] (BF$_4$)$_2$·n PPh$_3$ (n=2,3) prepared in situ (cf.: J. Am Chem. Soc. 103 4627–4629 (1981) and 104 3520–3522 (1982)). These catalysts, however, require strictly anhydrous reaction conditions (cf.: Transition metal catalyzed polymerizations; Alkenes and dienes, Part A, Edited by R. P. Quirk, 1983 pp. 341–354).

SUMMARY OF THE INVENTION

The present invention relates to a process for the preparation of dimerization products from aliphatic mono-olefins having 2 to about 12 carbon atoms characterized in that the aliphatic mono-olefin is contacted with a catalytic system formed by combining a palladium and/or ruthenium compound and an acid with a pKa of less than 2, except hydrohalogenic acids, in an aprotic organic solvent.

The presence of an acid as defined above in the catalytic system of the process of the invention may result in very high rates of dimerization by strong activating effects in an aprotic organic solvent.

DESCRIPTION OF THE PREFERRED EMBODIMENTS

Aliphatic mono-olefins having 2 to about 12 carbon atoms which can be used in the process according to the invention are linear or branched alkenes or cycloalkenes, such as for example ethene, propene, butene-1, butene-2, the isomeric pentenes, hexenes, octenes and dodecenes, cyclopentene, cyclooctene and cyclododecene. Examples of other aliphatic mono-olefins are substituted alkenes such as allyl alcohol, acrylic acid and alkyl-, aryl-, aralkyl esters of acrylic acid. The preferred olefins are ethene and propene.

It is to be pointed out that the term "dimerization products" as it is employed herein refers to olefin products obtained by reaction of two identical olefins as well as by the reaction of two different olefins, and to the alcohol, ether or ester derivatives of these olefin products obtained in-situ by the further presence of water, an alcohol or a carboxylic acid, respectively in the reaction mixture.

According to the invention, both homogeneous and heterogeneous catalysts can be used. The use of homogeneous catalysts is preferred.

The catalyst used in the process of the invention therefore preferably comprises palladium compounds and/or ruthenium compounds which are soluble in the reaction mixture or form in-situ soluble compounds therein.

Examples of suitable palladium compounds are palladium nitrate, palladium sulfate, palladium halides and palladium carboxylates, preferably carboxylates of carboxylic acids having not more than about 12 carbon atoms. Also palladium salts of acids with a pKa<2 as specified hereinafter can be used. Palladium carboxylates, in particular palladium acetate, are preferably used.

Further examples of suitable palladium compounds are palladium complexes such as bis(2,4-pentanedionato)palladium, bis(picolinato)palladium, tetrakis(-triphenylphosphine)palladium, tetrakisacetonitrile palladium tetrafluoroborate, bis(-tris-o-tolylphosphine)palladium acetate, bis(tri-phenylphosphine)palladium sulfate.

Examples of suitable ruthenium compounds are ruthenium (III) chloride, ruthenium IV chloride, ruthenium III chloride trihydrate, ruthenium oxides, ruthenium carboxylates such as ruthenium acetate or ruthenium propionate, ruthenium III tris acetylacetonate and organo ruthenium complexes with monodentate P and N ligands. Further, ruthenium salts of acids with a pKa of less than 2 as specified hereinafter may be suitable.

The quantity of the palladium and/or ruthenium compound used may very within wide ranges and is generally in the range between about $10^{-6}$ and about $10^{-1}$ and preferably in the range between about $10^{-5}$ and about $10^{-2}$ mol palladium and/or ruthenium compound per mol olefin starting material.

The acid with a pKa of less than 2 used in the process of the invention may comprise organic acids such as carboxylic acids and organic sulfonic acid as well as inorganic acids, which preferably have a noncoordinating anion by which is meant that little or no interaction takes place between the palladium and the anion. Typical examples of such anions are PF$_6^-$, SbF$_6^-$, BF$_4^-$ and ClO$_4^-$.

Acids preferably used are, for instance, perchloric acid, sulfuric acid, sulfonic acids and those acids that can be formed possibly in situ, by interaction of a Lewis acid such as, for example, BF$_3$, AsF$_5$, SbF$_5$, PF$_5$, TaF$_5$ or NbF$_5$ with a Broensted acid such as, for example, a hydrohalogenic acid, in particular HF, fluorosulfonic acid, phosphoric acid or sulfuric acid. Specific examples of the last-named type of acids are fluorosilicic acid, HPF$_4$, HSbF$_4$ and HBF$_4$, which is preferred. Typical sulfonic acids that can be used are fluorosulfonic acid, chlorosulfonic acid and the organic sulfonic acids such as, for example, methanesulfonic acid, 2-hydroxy-propane sulfonic acid, p-toluene sulfonic acid and trifluoromethane sulfonic acid, of which the last two acids are preferred.

Carboxylic acids which may be used are for example trifluoroacetic acid, trichloroacetic acid and dichloroacetic acid.

The quantity of the acid with a pKa of less than 2 may be at least 1 equivalent and is preferably at least 10 equivalent acid per gramatom palladium and/or ruthenium.

Further, when Group Va atoms containing ligands are used in the catalytic system, an excess of the acid relative to the ligands strongly activates the catalytic system. Accordingly, in the process of the invention, the catalytic system is formed by combining the palladium and/or ruthenium compound, a ligand containing at least one atom of Group Va of the Periodic System of Elements as coordinating atom and the acid with a pKa of less than 2 in a quantity of more than 1 equivalent acid per gramatom Group Va atom present in the ligand.

Monodentate ligands which may be used in the process of the invention comprise a compound containing one Group Va atom of the Periodic System of Elements, in particular a compound containing one trivalent N or P atom, which is bonded to at least one aromatic hydrocarbon group or a compound containing a trivalent N atom, which is a member of a heterocyclic aromatic ring.

Examples of suitable monodentate ligands comprising a compound which contains a trivalent N or P atom bonded to at least one aromatic hydrocarbon group are N,N'-dialkylanilines and phosphines such as N,N'-dimethylaniline, N,N'diethylaniline, N,N'-dibutylaniline, 4-chloro-N,N'-dimethylaniline, 4-ethoxy-N,N'-dimethylaniline, 4-dimethylaminobenzenesulfonic acid, 3-dimethylaminobenzenesulfonic acid, bis(1,1-dimethylethyl)phenylphosphine, dimethylphenylphosphine, cyclohexyldiphenylphosphine, dibutylphenylphosphine, methyldiphenylphosphine, triphenylphosphine, tris(4-chlorophenyl)phosphine, tris(4-methoxyphenyl)phosphine, tris(2-methoxyphenyl)phosphine, tris(4-butylphenyl)phosphine, tris(4-trisfluorophenyl)phosphine, tris(4-fluorophenyl)phosphine and 2-carboxyphenyl diphenylphosphine.

Examples of suitable monodentate ligands comprising a compound which contains a trivalent N atom being part of a heterocyclic aromatic ring are pyridines and quinolines such as pyridine, 2,6-di-methylpyridine, 4-ethylpyridine, 2-methoxypyridine, 2-chloropyridine, 3-chloropyridine, 2,6-dichloropyridine, 2-pyridine carboxylic acid, 3-pyridine carboxylic acid, quinoline, 2-methylquinoline and 2-chloroquinoline.

The use of a monodentate ligand which comprises N,N'-dimethylaniline, triphenylphonphine, pyridine or the derivatives thereof is preferred.

Chelate ligands which may be used in the process of the invention comprise a compound containing at least two atoms of Group Va of the Periodic System of Elements, which are connected through a chain comprising 2 to about 6 carbon atoms.

Examples of suitable chelate ligands comprise compounds containing two phosphorus atoms which are connected through a chain comprising 2 or 3 carbon atoms such as 1,2-ethanediylbisdiphenylphosphine, 1,2-ethenediylbisdiphenylphosphine, 1,2-phenylenebisdiphenylphosphine and 1,3-propanediylbisdiphenylphosphine.

Further examples of suitable chelate ligands comprise compounds containing two nitrogen atoms which are connected through a chain comprising 2 carbon atoms, in particular compound containing in the molecule a group of the formula

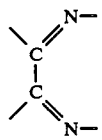

such as 1,10-phenanthroline, 4,7-dimethyl-1,10-phenanthroline, 4,7-diphenyl-1,10-phenanthroline-disulfonic acid, 2,2'-bipyridine, 4,4'-dimethyl-2,2-bipyridine and 4,4'-dichloro-2,2'bipyridine.

The quantity of ligand used for the catalyst in the process of the invention is at least about 1 mol ligand per gram atom palladium and/or ruthenium.

The process according to the invention is carried out in an aprotic organic solvent. Examples of suitable solvents are hydrocarbons such as hexane, cyclohexane, octane, cyclo-octene, benzene, toluene, the xylenes, ethylbenzene and cumene, halogenated hydrocarbons such as chloroform, 1,2-dichloroethane, perfluoroalkanes, chlorobenzene and dichlorobenzene, ethers such as tetrahydrofuran, dimethylether or diethylene glycol (diglyme), methyl-t-butylether and dioxane, and nitro compounds such as nitromethane and nitrobenzene.

Reactant olefins may also function as an aprotic solvent especially when higher olefins or substituted olefins such as for example esters of acrylic acid are used.

The use of aromatic hydrocarbons and halogenated aliphatic hydrocarbons as solvent is preferred.

As mentioned earlier, the dimerization products of the process of the invention may comprise an alcohol, ether or ester obtained in-situ by the presence of water, an alcohol or carboxylic acid, respectively. The alcohols or carboxylic acids which may be present are preferably lower aliphatic alcohols and carboxylic acids such as methanol, ethanol, propanol, acetic acid, propionic acid or caproic acid. The quantity of water, alcohol or carboxylic acid present should be such that the aprotic properties of the reaction medium dominates, i.e. a quantity below about 50%v and preferably below 20%v calculated on the quantity of the aprotic solvent.

The process according to the present invention can be carried out at temperatures of up to about 200° C. and preferably in the range between about 20° C. and about 135° C. The pressure lies between about 1 and about 100, in particular between about 20 and about 75 bar gauge.

The process according to the invention can be carried out batchwise, semi-continuously or continuously.

The process according to the invention is hereinafter illustrated on the basis of practical examples, which are provided for illustrative purposes and are not to be construed as limiting the invention.

EXAMPLE 1

A 300 ml magnetically stirred Hastelloy C autoclave ("Hastelloy" is a trade mark) was charged with 50 ml solvent, 0.1 mmol palladium acetate or ruthenium (acetylacetonate) and an acid with a pKa of less than 2 as catalytic system. The autoclave was flushed with ethene, filled with ethene at a pressure of 40 bar, sealed and heated to a specified temperature. After a specified reaction time the contents of the autoclave were analyzed by gas/liquid chromatography.

The conversion of ethane to products (dimers, trimers, etc.) was calculated as mol ethene per gramatom palladium or ruthenium per hour. The selectivity to the butenes is given as % mol butenes in the products formed.

Data and results of the experiments 1-6 carried out according to the above are indicated in Table I.

In an experiment not according to the invention, a glass-lined autoclave was charged with 50 ml toluene and 5 mmol trifluoromethane sulfonic acid. The autoclave was flushed with ethene and filled with ethene at a pressure of 40 bar and heated to 70° C. After a reaction time of 5 hours only traces of dimers appeared to be formed on analysis by gas/liquid chromatography. This experiment shows that under comparable reaction conditions dimerization is not effected by the presence of an acid with a pKa of less than 2 without the presence of a palladium or ruthenium compound.

Data and results of the experiments 1-9 carried out according to the above are indicated in Table II. In experiment 2, the composition of the formed butenes was analyzed as: butene-1 24%, trans. butent-2 47.7%, cis-butene-2 38.3%. In experiment 9, the composition of the formed butenes was analyzed as: butene-1 6.3%, trans-butene-2 63.3%, cis-butene-2 30.7%. The experiments 4, 6 and 8 are not according to the invention and show that an excess of the acid with a pKa of less than 2 relative to the ligand is required for a high conversion.

TABLE II

| Exp. No. | Catalyst 0.1 mmol Pd—acetate + ligand (mmol) | | Acid with PKa <2 (mmol) | | Solvent | Ethene Bar | Reaction Temperature | Reaction Time | Conversion mol $C_2H_2$/gram-atom Pd/hour | Selectivity |
|---|---|---|---|---|---|---|---|---|---|---|
| 1 | triphenylphosphine | (0.1) | p-toluene-sulfonic acid | (10) | toluene | 40 | 70 | 1 | 900 | 96 |
| 2 | pyridine | (3) | $CF_3SO_3H$ | (5) | toluene | 40 | 80 | 1 | 900 | 94 |
| 3 | 2,2'-bipyridine | (1) | $CF_3SO_3H$ | (4) | toluene | 40 | 70 | 1 | 5000 | 93 |
| 4 | 2,2'-bipyridine | (2) | $CF_3SO_3H$ | (4) | toluene | 40 | 75 | 1 | traces | |
| 5 | triphenylphosphine | (3) | $CF_3SO_3H$ | (4) | toluene | 40 | 95 | 1 | 5000 | 97 |
| 6 | triphenylphosphine | (3) | $CF_3SO_3H$ | (2) | toluene | 40 | 105 | 5 | 80 | 100 |
| 7 | 2-carboxyphenyldiphenylphosphine | (1.5) | $HBF_4$ | (4) | chloroform | 20 | 110 | 0.5 | 3000 | 98 |
| 8 | 2-carboxyphenyldiphenylphosphine | (1.5) | $HBF_4$ | (1) | chloroform | 20 | 100 | 5 | 60 | 98 |
| 9 | N,N'—dimethylaniline | (3) | $CF_3SO_3H$ | (5) | toluene | 40 | 75 | 0.7 | 7000 | 93 |

EXAMPLE 3

A 300 ml magnetically stirred Hastelloy C autoclave ("Hastelloy" is a trade mark) was charged with a solvent and palladium acetate a monodentate ligand and an acid with a pKa of less than 2 as catalytic system. The autoclave was flushed with propene, filled with 40 ml liquid propene, sealed and heated to a specified temperature. After a specified reaction time the contents of the autoclave were analyzed by gas/liquid chromatography.

The conversion of propene to products (dimers, trimers, etc.) was calculated as mols of propene per gramatom palladium per hour. The selectivity to the dimer hexenes is given as % mol dimers in the products formed.

Data and results of the experiments 1 and 2 carried out according to the above are mentiond in Table III.

TABLE I

| Experiment No. | Catalyst | Acid with pKa <2 (mmol) | | Solvent | Reaction Temperature, °C. | Reaction Time Hr. | Conversion mol $C_2H_4$/gramatom Pd or Ru/hour | Selectivity, % mol |
|---|---|---|---|---|---|---|---|---|
| 1 | Pd—acetate | $CF_3SO_3H$ | (5) | toluene | 75 | 1 | 4600 | 93 |
| 2 | Pd—acetate | $CF_3SO_3H$ | (5) | toluene | room temperature | 3 | 900 | 94 |
| 3 | Pd—acetate | $CF_3SO_3H$ | (5) | dichlorobenzene | 75 | 1 | 4500 | 93 |
| 4 | Pd—acetate | $CF_3SO_3H$ | (5) | diglyme | 70 | 5 | 350 | 93 (butene-1 69%) |
| 5 | Pd—acetate | p-toluene sulfonic acid | (5) | toluene | 70 | 5 | 600 | 96 |
| 6 | Pd—acetate | $CF_3SO_3H$ | (4) | hexane | 70 | 0.5 | 5000 | 95 |
| 7 | Ru—(acetylacetonate) | $CF_3SO_3H$ | (5) | toluene | 60 | 0.7 | 8000 | 95 |

EXAMPLE 2

A 300 ml magnetically stirred Hastelloy C autoclave ("Hastelloy" is a trade mark) was charged with 50 ml solvent and 0.1 mmol palladium acetate, a ligand, and an acid with a pKa of less than 2 as catalytic system. The autoclave was flushed with ethene, filled with ethene at a specified pressure, sealed and heated to a specified temperature. After a specified reaction time the contents of the autoclave were analyzed by gas/liquid chromatography.

The conversion of ethene to products (dimers, timers, etc.) was calculated as mol ethene per gramatom palladium per hour. The selectivity to butenes is given as % mol butenes in the product formed.

TABLE III

| Exp. No. | Pd Acetate (mmol) | Monodentate Ligand (mmol) | | Acid with pKa <2 (mmol) | | Solvent (ml) | Reaction Temperature | Reaction Time | Conversion mol/ gramatom Pd/hr. | Selectivity % mol |
|---|---|---|---|---|---|---|---|---|---|---|
| 1 | 0.1 | triphenylphosphine | (3) | $CF_3SO_3H$ | (4) | toluene (50) | 90 | 5 | 30 | 98 |

TABLE III-continued

| Exp. No. | Pd Acetate (mmol) | Monodentate Ligand (mmol) | | Acid with pKa <2 (mmol) | | Solvent (ml) | Reaction Temperature | Reaction Time | Conversion mol/ gramatom Pd/hr. | Selectivity % mol |
|---|---|---|---|---|---|---|---|---|---|---|
| 2 | 0.1 | 2-carboxyl- phenyldi- phenylphos- phine | (1.5) | HBF₄ | (4) | chloro- form (50) | 100 | 5 | 20 | 95 |

EXAMPLE 4

A 300 ml magnetically stirred Hastelloy C autoclave ("Hastelloy" is a trade mark) was charged with 40 ml toluene, 10 ml acetic acid and 0.1 mmol palladium acetate and 4 mmol $CF_3SO_3H$ as catalytic system. The autoclave was flushed with ethene and filled with ethene at a pressure of 40 bar, sealed and heated to 70° C. After a reaction time of 1 hour the contents of the autoclave were analyzed by gas/liquid chromatography.

The conversion of ethene to dimerization products was 4800 mol ethene per gramatom palladium per hour. The conversion of acetic acid to sec.butyl acetate was 70% mol.

EXAMPLE 5

A 300 ml magnetically stirred Hastelloy C autoclave ("Hastelloy" is a trade mark) was charged with 50 ml methylacrylate and 0.5 mmol ruthenium acetylacetonate, 0.5 mmol 1,3-propane-diylbis-di-phenylphosphine and 3 mmol trifluoromethanesulfonic acid as catalytic system. The autoclave was flushed with ethene and filled with ethene at a pressure of 40 bar, sealed and heated to 90° C. After a reaction time of 5 hours the contents were analyzed by gas/liquid chromatography.

The conversion of methylacrylate was 40% mol. The composition of the product mixture was methyl pentenoates 30% mol,
butenes 30% mol,
acrylate dimers 40% mol.

EXAMPLE 6

A 300 ml magnetically stirred Hastelloy C autoclave ("Hastelloy" is a trade mark) was charged with 50 ml methylacrylate and 0.5 mmol palladium acetate, 1 mmol triphenylphosphine and 3 mmol trifluoromethanesulfonic acid as catalytic system. The autoclave was flushed with ethene and filled with ethene at a pressure of 40 bar, sealed and heated to 70° C. After a reaction time of 1 hour the contents were analyzed by gas/liquid chromatography.

The conversion of methylacrylate was 30% mol. The composition of the product mixture was methyl pentenoates 43% mol,
butenes 46% mol,
acrylate dimers 11% mol.

I claim as my invention:

1. A process for the preparation of dimerization products from aliphatic mono-olefins having 2-12 carbon atoms which process comprises contacting the aliphatic mono-olefin with a catalytic system formed by combining a palladium and/or ruthenium compound and an acid with a pKa of less than 2, except hydrohalogenic acids, in an aprotic organic solvent.

2. The process of claim 1 wherein the acid with a pKa of less than 2 is $HBF_4$.

3. The process of claim 1 wherein the acid with a pKa of less than 2 is a sulfonic acid.

4. The process of claim 3 wherein the acid with a pKa of less than 2 is a trifluoromethane sulfonic acid or p-toluenesulfonic acid.

5. The process of claim 1 wherein the catalytic system is formed by combining the palladium and/or ruthenium compound, a ligand containing at least one atom of the Group Va of Periodic System of Elements as coordinating atom and the acid with a pKa of less than 2 in a quantity of more than 1 equivalent acid per gram atom Group Va atom present in the ligand.

6. The process of claim 5 wherein the ligand is a monodentate ligand which comprises a compound containing one trivalent N or P atom which is bonded to at least one aromatic hydrocarbon group.

7. The process of claim 6 wherein the monodentate ligand comprises N,N'-dimethylaniline or a derivative thereof.

8. The process of claim 6 wherein the monodentate ligand comprises triphenylphosphine or a derivative thereof.

9. The process of claim 6 wherein the monodentate ligand comprises a compound containing a trivalent N atom, which is a member of a heterocyclic aromatic ring.

10. The process of claim 9 wherein the monodentate ligand comprises pyridine or a derivative thereof.

11. The process of claim 5 wherein the ligand is a chelate ligand which comprises a compound containing at least two atoms of Group Va of the Periodic System of Elements, which are connected through a chain comprising 2-6 carbon atoms.

12. The process of claim 11 wherein the chelate ligand comprises a compound which contains in the molecule a group of the formula

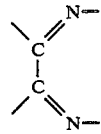

13. The process of claim 5 wherein the quantity of ligand is at least 1 mol ligand per gram atom palladium and/or ruthenium.

14. The process of claim 1 wherein the quantity of the acid with a pKa of less than 2 is at least 10 equivalent acid per gram atom palladium and/or ruthenium.

15. The process of claim 1 wherein the aliphatic mono-olefin is ethene.

16. The process of claim 1 wherein the aliphatic mono-olefin is propene.

* * * * *

UNITED STATES PATENT AND TRADEMARK OFFICE
CERTIFICATE OF CORRECTION

PATENT NO.   : 4,599,476
DATED        : July 8, 1986
INVENTOR(S)  : Eit Drent

It is certified that error appears in the above-identified patent and that said Letters Patent are hereby corrected as shown below:

On the cover page of the patent below the line "[30] Foreign Application Priority Data" should read:

December 19, 1984 [GB] United Kingdom.

Signed and Sealed this

Twenty-ninth Day of March, 1988

Attest:

DONALD J. QUIGG

Attesting Officer

Commissioner of Patents and Trademarks